United States Patent [19]

Jander

[11] 4,020,697

[45] May 3, 1977

[54] GAS SAMPLING PROBE

[76] Inventor: Berthold R. Jander, 3000 W. Irving Blvd., Apt. 110, Irving, Tex. 75061

[22] Filed: Nov. 10, 1975

[21] Appl. No.: 630,289

[52] U.S. Cl. .................. 73/421.5 R; 73/40.5 R
[51] Int. Cl.² .................................... G01N 1/22
[58] Field of Search ............... 73/421.5 R, 40.5 R, 73/40.7, 23

[56] References Cited

UNITED STATES PATENTS

| | | | |
|---|---|---|---|
| 2,386,832 | 10/1945 | Zaikowsky et al. | 73/421.5 R |
| 2,742,266 | 4/1956 | Voelkerding | 73/40.5 R X |
| 3,084,553 | 4/1963 | Cullinan et al. | 73/421.5 R |
| 3,106,089 | 10/1963 | Scott et al. | 73/40.5 R |
| 3,198,265 | 8/1965 | Voelkerding | 73/421.5 R X |
| 3,343,421 | 9/1967 | Miller | 73/421.5 R |
| 3,490,288 | 1/1970 | Patnode | 73/421.5 R |
| 3,610,048 | 10/1970 | Weeks | 73/421.5 R |
| 3,943,750 | 3/1976 | McLaughlin | 73/421.5 R X |

FOREIGN PATENTS OR APPLICATIONS

| | | | |
|---|---|---|---|
| 76,994 | 1/1954 | Denmark | 73/421.5 R |
| 918,381 | 8/1954 | Germany | 73/40.5 R |

*Primary Examiner*—Richard C. Queisser
*Assistant Examiner*—Joseph W. Roskos
*Attorney, Agent, or Firm*—Richards, Harris & Medlock

[57] ABSTRACT

Disclosed is a probe for use in obtaining gas samples from around subsurface conduit systems. The probe has an elongate body with a chamber extending through the length of said body. A threaded reduced diameter portion is formed on the rearmost end of the body for use in attaching the probe to a length of conduit. A shoulder is formed adjacent to the threaded portion and has a diameter slightly larger than the conduit to which the probe is attached. The shoulder is adjacent to an enlarged portion with an arcuate periphery. A reduced diameter portion is formed adjacent to the enlarged portion. A plurality of bores extend through the reduced diameter portion from various directions and communicate with the axial chamber in the body. A bulbous portion is formed on the forwardmost end of the probe adjacent to the reduced diameter portion.

2 Claims, 4 Drawing Figures

GAS SAMPLING PROBE

BACKGROUND OF THE INVENTION

The present invention relates to probes for use with systems for detecting underground gas leaks from conduit systems. More particularly, the present invention relates to improvements in gas probes which are inserted into the ground for sampling subsurface gases.

In conventional systems for detecting leaks in underground conduit system, it is common to utilize gas detectors for locating underground leaks. The testers involve the use of a probe for sampling underground gases which is connected through a conduit to a gas detection device. A typical gas detection is the D-15 Gastester manufactured by Scott Davis Instruments of Lancaster, New York.

When underground conduits are present, it is necessary to gain access to the area surrounding these underground conduits. A small opening which terminates on the exterior surface of the conduit is formed in the soil. This can be accomplished using a impact bar. Thereafter, a probe on the end of the length of the conduit is inserted through the opening to a point adjacent to the underground conduit. A sample of the underground gas adjacent to the conduit is collected through the probe and is transported up through the conduit to the gas tester device to determine the presence of undesirable gases which would be present around a gas leak.

Although these conventional systems detect gas leaks in many environments, they have not been entirely satisfactory under all conditions of service because of the tendency of conventional gas probes to plug up during insertion into the ground. This is especially true when the operation is being performed in moist soils which easily extrude into the probe.

SUMMARY OF THE PRESENT INVENTION

Therefore, according to the preset invention, an improved probe is provided having arcuate guide surfaces on the periphery thereof for guiding the probe down in through the opening in the ground and maintaining the orifices in the probe spaced away from the walls of the wall cavity.

According to a particualr feature of the present invention, a improved gas probe is provided having an elongate body and enlarged arcuate portions spaced on either side of a reduced diameter portion. A threaded portion is formed on one end of the probe for connection to a conduit. A chamber extends through the center of the body. Bores are formed in the reduced diameter portion and communicate with the chamber.

BRIEF DESCRIPTION OF THE DRAWINGS

The advantages and features of the present invention will become more apparent from a understanding of the description when considered in connection with the accompanying Drawings in which.

BRIEF DESCRIPTION OF THE PREFERRED EMBODIMENT

Figure 1:
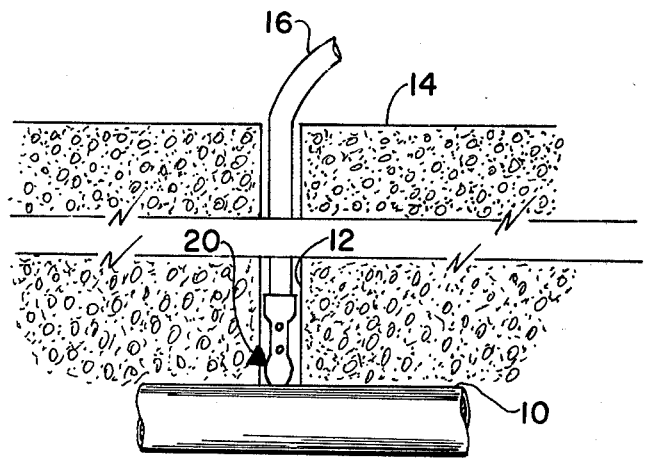
FIG. 1 is a partial sectional view illustrating the use of the improved probe of the present invention to detect gases adjacent to a buried conduit.

Referring now to the Drawings, wherein like reference characters designate like or corresponding parts throughout the several views, there is illustrated in FIG. 1, a portion of a buried conduit system 10. For purposes of disclosure of the present invention, it is assumed that it is necessary to determine whether a leak is present in the buried conduit system 10 in the vicinity of the area illustrated. To accomplish this, an impact bar is driven into the ground to form a passageway 12 which extends from the ground surface 14 to an area adjacent to the conduit 10. These passageways are typically 5/8% in diameter, depending upon the size of the device utilized in the formation thereof.

For detection of a gas leak, an improved probe 20 of the present invention is inserted down through the passageway 12 while connected to a length of conduit 16. Conduit 16 is in turn connected to a gas detector. An example of a typical gas detector is one manufactured by Scott Davis Instruments having model No. D-15, Gastester. A flexible aspirator bulk is used to cause a vacuum in the conduit 16, causing the flow of gases from the probe 20 through the conduit 16 to the gas detector. Thus, it is important that the orifices in the probe 20 remain free from blockage of soil or other materials.

Figure 2:
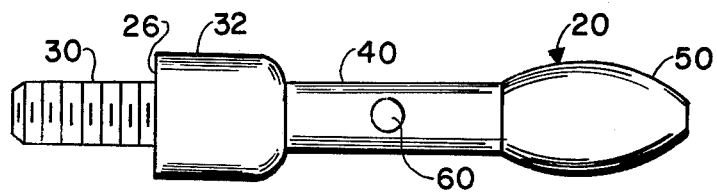
FIG. 2 is a side elevation of the improved probe of the present invention.
Figure 3:
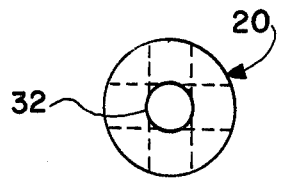
FIG. 3 is an end view of the improved probe of the present invention.
Figure 4:
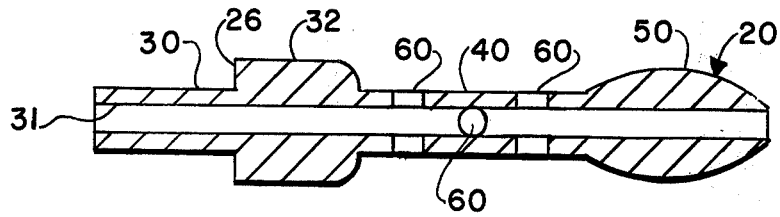
FIG. 4 is a longitudinal section of the device illustrated in FIG. 2.

The details of the improved probe 20 of the present invention are illustrated in FIGS 2–4. Probe 20 is constructed from metallic plastic or other materials and has a reduced diameter threaded portion 30 formed on one end thereof. A central passageway 31 extends through probe 20 and is open at both ends thereof. A shoulder 26 is formed adjacent to the reduced diameter threaded portion 30 and provides a surface against which the fitting connecting conduit 16 to the threaded portion 30 can abut. It is to be understood, of course, that suitable threads are formed on the reduced diameter portion 30 which mate with the conduit 16. It is envisioned, of course, that the portion 30 could be formed in other shapes to facilitate connection to the conduit 16.

Formed adjacent to the shoulder 26 is an enlarged portion 32 with smooth arcuate peripheral surfaces for contacting and sliding along a wall of the passageway 12. A reduced diameter portion 40 is formed adjacent to the portion 32. A bulbous portion 50 is formed on the end opposite the threaded portion 30 and has substantially the same diameter as the portion 32. A plurality of radially extending bores 60 are formed in the reduced diameter portion 40 to communicate with the exterior of the probe and passageway 32.

In operation, when the probe is inserted into the passageway, the reduced diameter portion 40 forms an annular space with the wall of the passageway from which gas can be asperated during the gas sampling process. In addition, the two enlarged portions prevent the bores 60 from becoming clogged during insertion of the probe into the passageway.

Thus the present invention discloses an improved probe structure for use in muddy soils, and the like, which minimizes the clogging effect of soils while obtaining gas samples from the vicinity of underground conduit systems.

Having thus described the invention, it has become apparent to those of ordinary skill in the art that the present invention may be practiced other than as spe- cifically described herein and that numerous alterations, modifications, and the like, can be made by those who have ordinary skill in the art without departing from the spirit and scope of the invention as set forth in the appended claims.

What is claimed is:

1. A gas probe for attachement to a conduit for inserting in a pre-existing hole to obtain gas samples from the vicinity of a buried gas system comprising:
    an elongate body of a size to fit in said hole;
    means on one end of said body for attaching said body to the conduit to communicate with said probe when said probe is inserted in said hole;
    two enlarged portions on said body positioned on either side of a reduced diameter portion, said enlarged portions having arcuate peripheral surface thereon for engaging the walls of said hole during insertion and removal of the probe from said hole whereby said probe is centered in said hole and said enlarged portions act as guides to reduce lodging of soil in the sampling bores in the body;
    a chamber in said body for communication with the conduit;
    said reduced diameter portion having sampling bores formed therein communicating with said chamber; and
    a sampling bore formed in said body on the end opposite said one end and communicating with said chamber.

2. The probe of claim 1 wherein said means for attaching conduit comprises threads on said one end.

* * * * *

UNITED STATES PATENT OFFICE
CERTIFICATE OF CORRECTION

Patent No. 4,020,697  Dated May 3, 1977

Inventor(s) Berthold R. Jander

It is certified that error appears in the above-identified patent and that said Letters Patent are hereby corrected as shown below:

Col. 1, line 11, "system" should be --systems--;
      line 22, "a" should be --an--;
      line 39, "preset" should be --present--;
      line 47, "a improved" should be --an improved--;
      line 57, "a" should be --an--.

Col. 2, line 15, "5/8%" should be --5/8"--;
      line 23, "bulk" should be --bulb-- .

Col. 3, line 7, "attachement" should be --attachment--;
    3 and 4, lines 16 and 1 respectively, "surface" should be --surfaces--.

Signed and Sealed this ninth Day of August 1977

[SEAL]

Attest:

RUTH C. MASON
Attesting Officer

C. MARSHALL DANN
Commissioner of Patents and Trademarks